United States Patent [19]
Henry

[11] Patent Number: 5,980,467
[45] Date of Patent: Nov. 9, 1999

[54] NUTRITIONAL DEFICIENCY IDENTIFICATION SYSTEM

[76] Inventor: James D. Henry, 6051 Brandy Run Rd. South, Mobile, Ala. 36608

[21] Appl. No.: 09/073,865

[22] Filed: May 7, 1998

[51] Int. Cl.$^6$ ........................................................ A61B 5/00
[52] U.S. Cl. ............................................ 600/549; 600/301
[58] Field of Search ................................... 600/549, 301; 364/413.2; 368/10

*Primary Examiner*—Max Hindenburg
*Assistant Examiner*—Brian Szmal
*Attorney, Agent, or Firm*—Jack Lo

[57] ABSTRACT

A nutritional deficiency identification system includes a temperature sensor connected to a biofeedback instrument, which is connected to a computer. At a testing site, the sensor is attached to a subject, and an evaluation test is performed under software control. The subject's temperature is monitored, displayed, and recorded at regular intervals during the entire evaluation. The beginning of the test comprises a temperature stabilization period in which the subject's body temperature is allowed to stabilize in the testing site's environment. After the stabilization period, a first nutritional supplement is placed on the subject's tongue at the beginning of a testing period. At an intermediate time during its testing period, the supplement is discarded, and the testing period is continued. The subject's metabolic and physiological responses to the supplement are reflected in body temperature fluctuations. After the testing period of the first supplement, another supplement is placed on the tongue at the beginning of another testing period. Additional supplements are similarly tested in sequence. The recorded temperature readings are uploaded to a server at an evaluation center, where they are analyzed by a health professional. For each nutritional supplement, a low number of temperature fluctuations during its testing period indicates that there is probably no nutritional need for it, whereas a higher number of temperature fluctuations indicates that there is probably a nutritional need for it.

15 Claims, 8 Drawing Sheets

| | |
|---|---|
| 01 | Antronex |
| 02 | Thymus PMG |
| 03 | Cal-Ma-Plus |
| 04 | Drenatrophin PMG |
| 05 | Gastrex Capsules |
| 06 | Cholacol II |
| 07 | Dermatrophin PMG |
| 08 | Arginex |
| 09 | Fen-Gre |
| 10 | Cataplex B |
| 11 | Hepatrophin PMG |
| 12 | B6-Niacinamide |
| 13 | Hypothalamus PMG |
| 14 | Cataplex B12 |
| 15 | Zymex II |
| 16 | Betacol |
| 17 | Mammary PMG (FEMALE) |
| 18 | Betafood |
| 19 | Myotrophin PMG |
| 20 | Black Currant Seed Oil |
| 21 | Neurotrophin PMG |
| 22 | Calcium Lactate |
| 23 | Oculotrophin PMG |
| 24 | Zinc Liver Chelate |
| 25 | Orchic PMG (MALE) |
| 26 | Choline |
| 27 | Ostrophin PMG |
| 28 | Collagen C |
| 29 | Ovatrophin PMG (FEMALE) |
| 30 | Collinsonia Root |

NUTRITIONAL DEFICIENCY IDENTIFICATION SYSTEM

BACKGROUND OF THE INVENTION

1. Field of the Invention

This invention relates generally to systems for identifying nutritional deficiencies.

2. Prior Art

Humans require many different nutrients for survival and health. There are a variety of factors that may influence an individual's nutritional needs, such as genetics, heredity, exposure to toxins, diet, physiological or psychological stress, activity level, age, weight, etc. There has been no reliable method for detecting such deficiencies, so they are usually discovered only when serious health problems develop.

OBJECTS OF THE INVENTION

Accordingly, the object of the present invention is to identify the nutritional needs or deficiencies of individuals. Further objects of the present invention will become apparent from a consideration of the drawings and ensuing description.

BRIEF SUMMARY OF THE INVENTION

A nutritional deficiency identification system includes a temperature sensor connected to a biofeedback instrument, which is connected to a computer. At a testing site, the sensor is attached to a subject, and an evaluation test is performed under software control. The subject's temperature is monitored, displayed, and recorded at regular intervals during the entire evaluation. The beginning of the test comprises a temperature stabilization period in which the subject's body temperature is allowed to stabilize in the testing site's environment. After the stabilization period, a first nutritional supplement is placed on the subject's tongue at the beginning of a testing period. At an intermediate time during its testing period, the supplement is discarded, and the testing period is continued. The subject's metabolic and physiological responses to the supplement are reflected in body temperature fluctuations. After the testing period of the first supplement, another supplement is placed on the tongue at the beginning of another testing period. Additional supplements are similarly tested in sequence. The recorded temperature readings are uploaded to a server at an evaluation center, where they are analyzed by a health professional. For each nutritional supplement, a low number of temperature fluctuations during its testing period indicates that there is probably no nutritional need for it, whereas a higher number of temperature fluctuations indicates that there is probably a nutritional need for it.

DETAILED DESCRIPTION OF THE INVENTION

Figures 1, 2:
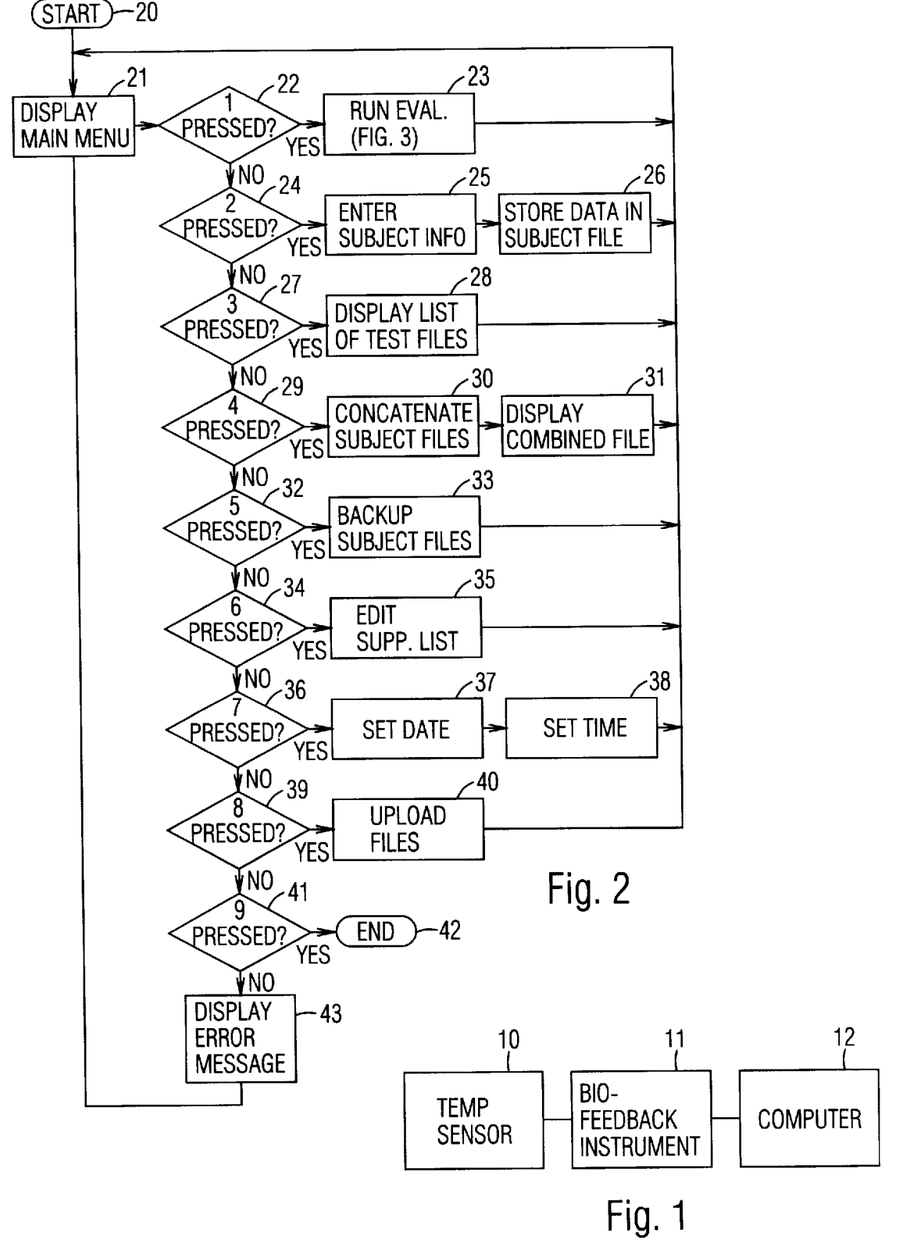
FIG. 1 is a block diagram of the present nutritional deficiency identification system.
FIG. 2 is a flowchart of a main menu of the system.

FIG. 1

A preferred embodiment of the invention is shown in the block diagram in FIG. 1. It comprises a temperature sensor 10 connected to a conventional biofeedback instrument 11, which is connected to a computer 12. Biofeedback instrument 11 may of be any suitable type that monitors body temperature, such as the model "TEMP/SC 201T" from Thought Technology, Ltd., which is made for connecting to a communication port of a personal computer. Computer 12 may also be of any suitable type, such as an IBM-compatible personal computer running the "MS-DOS" operating system. Temperature sensor 10 is preferably attached to a subject at the axillary area (armpit). A nutritional deficiency evaluation is performed with software loaded in computer 12.

Before the evaluation, the subject shall preferably prepare as follows:

A. Drink at least 2–3 glasses of good quality water per day for a week before the test.

B. Discontinue all nutritional supplements 7–10 days before the test.

C. Do not eat or drink anything after midnight the night before the test.

D. Sleep well the night before the test.

E. Do not exercise the morning of the test.

F. One hour before the test, eat two "EGGO OAT BRAN WAFFLES" with raw honey and butter, and drink only one cup of liquid—water, fruit juice, or herb tea.

FIG. 2

A flowchart of a main menu of the present software is shown in FIG. 2. After the start at block 20, a main menu is displayed at block 21. The main menu includes 9 selections numbered 1–9. If the "1" key is pressed at block 22, the nutritional deficiency evaluation test is performed at block 23, which is described in conjunction with FIG. 3. If the "2" key is pressed at block 24, a subject information screen is displayed at block 25 for entering the subject's information, which is stored in a subject file at block 26. If the "3" key is pressed at block 27, a list of previously-run test files is displayed at block 28. If the "4" key is pressed at block 29, the subject's information file and test file, which is created after a test, are concatenated or combined at block 30, and the combined file is displayed at block 31. If the "5" key is pressed at block 32, the subject's files are backed up at block 33. If the "6" key is pressed at block 34, a list of selected supplements is displayed for editing at block 35. If the "7" key is pressed at block 36, the date is displayed for editing at block 37, and the time is displayed for editing at block 38. If the "8" key is pressed at block 39, the subject's files are uploaded at block 40 to a server at an evaluation center, where a health professional will analyze the test results and determine if any supplements are to be prescribed. If the "9" key is pressed at block 41, the program is ended at block 42. If any other key is key pressed, an error message is displayed at block 43, and the process is returned to the main menu at block 21. FIGS. 3–9

Figure 3:
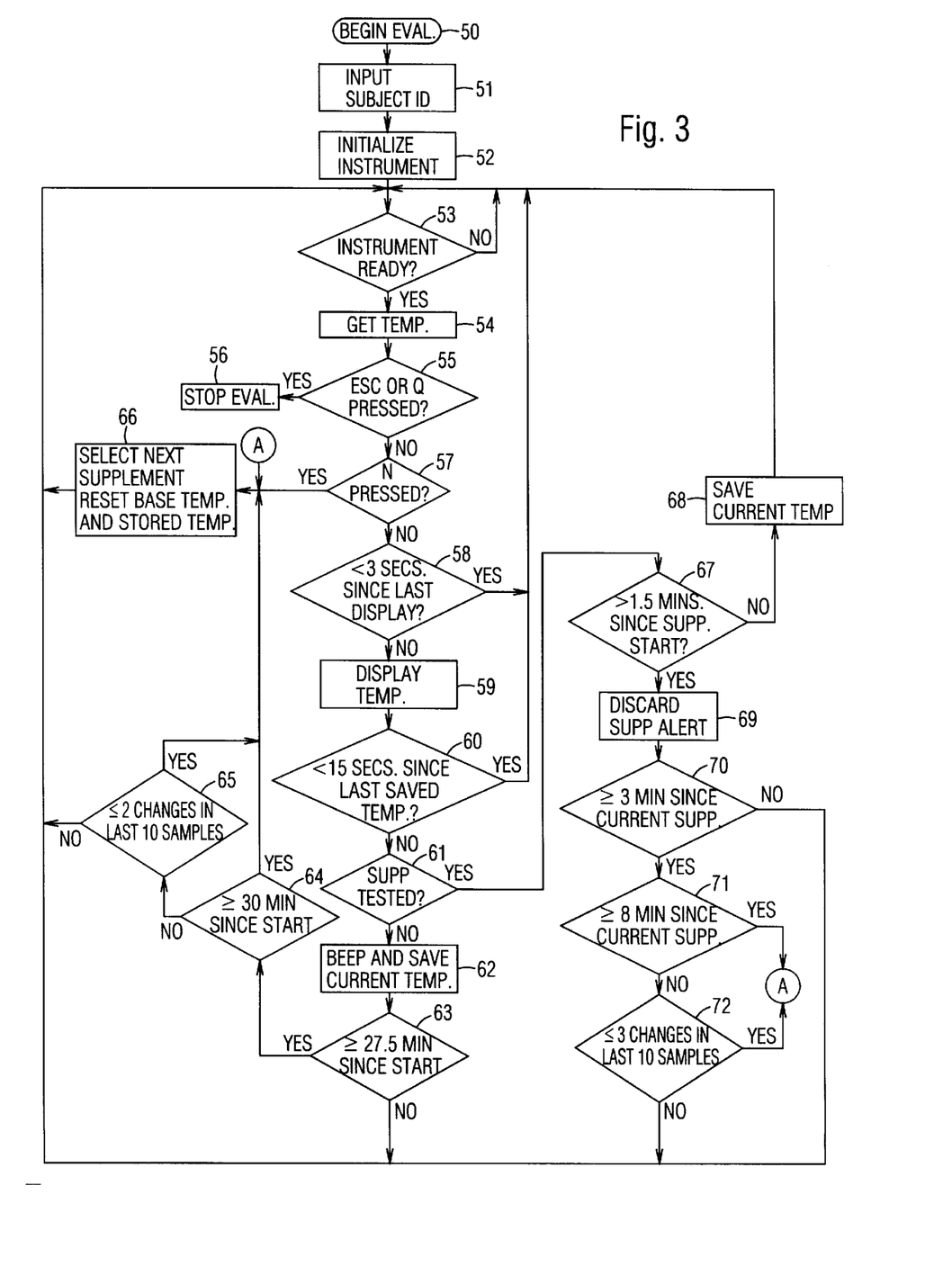
FIG. 3 is a flowchart of a nutritional supplement evaluation process of the system.
Figure 5:
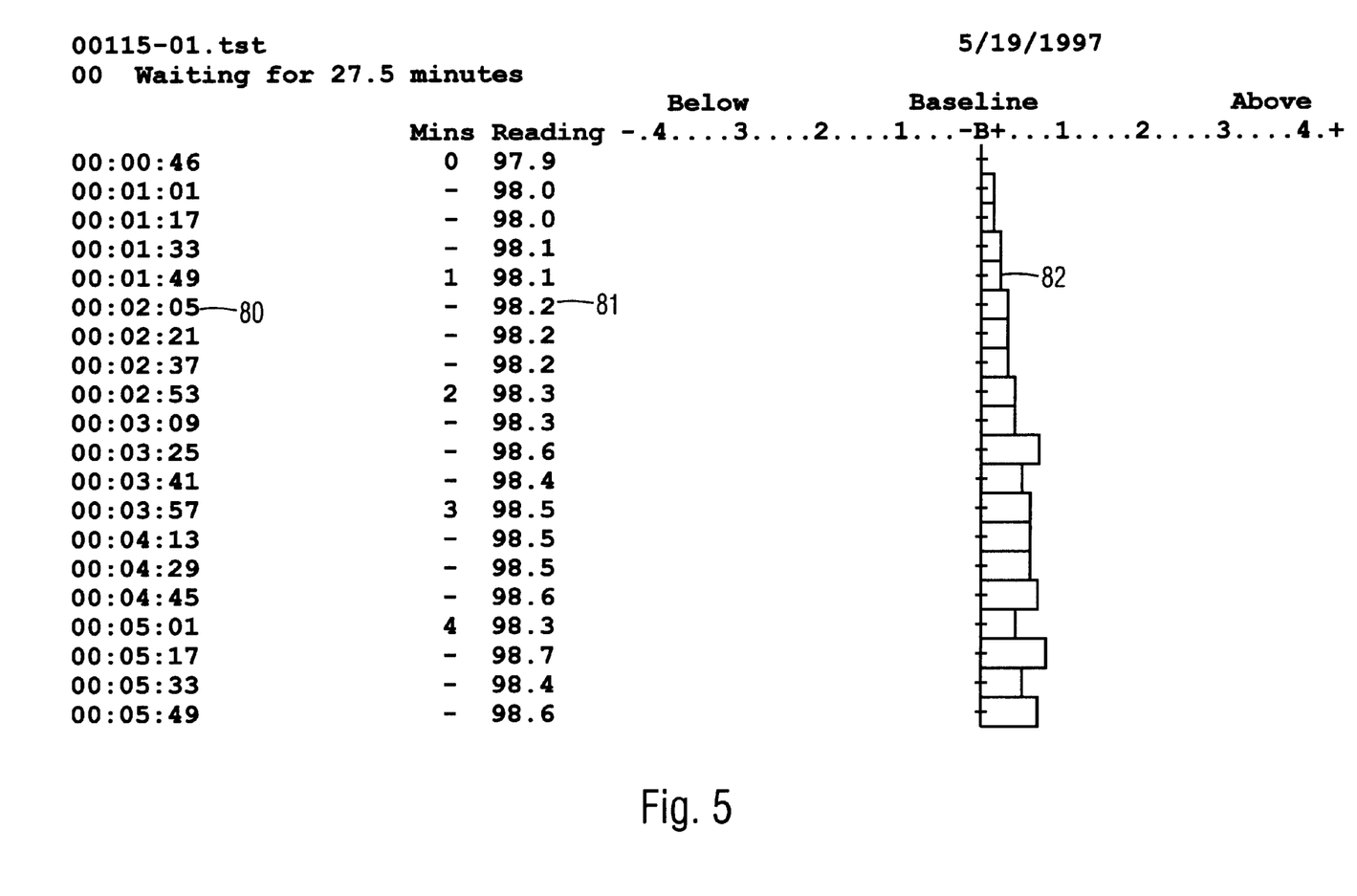
FIG. 5 is a temperature stabilization period screen showing the initial fluctuating temperature readings of a subject.

The detailed process flow of the nutritional deficiency evaluation test is shown in the flowchart in FIG. 3. When the evaluation is selected to be run (block 23 in FIG. 2), it is begun at block 50. The subject's identification is entered at block 51, and the biofeedback instrument is initialized at block 52. If the instrument is not ready at block 53, the process is returned to block 53. When the instrument is ready at block 53, a temperature reading is taken at block 54. If the "ESC" or "Q" key is pressed at block 55, the evaluation is stopped at block 56. If the "N" key is not pressed at block 57, but less than 3 seconds have elapsed since the previous temperature is displayed at block 58, the process is returned to block 53. The "N" key can be pressed to skip any particular supplement. If more than 3 seconds have elapsed at block 58, the current temperature is displayed at block 59 to an accuracy of 0.1 degrees, as shown in FIG. 5. If less than 15 seconds have elapsed since a previously saved temperature reading at block 60, the process is returned to block 53. If more than 15 seconds have elapsed at block 60, but a supplement is not confirmed as being tested at block 61, a beep is produced and the current temperature is saved at block 62. The rows of temperature readings in FIG. 5 are thus saved or recorded about 15 seconds apart. The bottom row of temperature reading, which represents the current temperature, is thus updated every 3 seconds, but it is not saved until 15 seconds after the previously saved temperature. Elapsed times 80 are shown in the left column, and temperature readings 81 are shown in the right column. The first temperature reading is taken as a baseline in a bar graph 82, and the other temperature readings are shown as fluctuations relative to the baseline.

Figure 6:
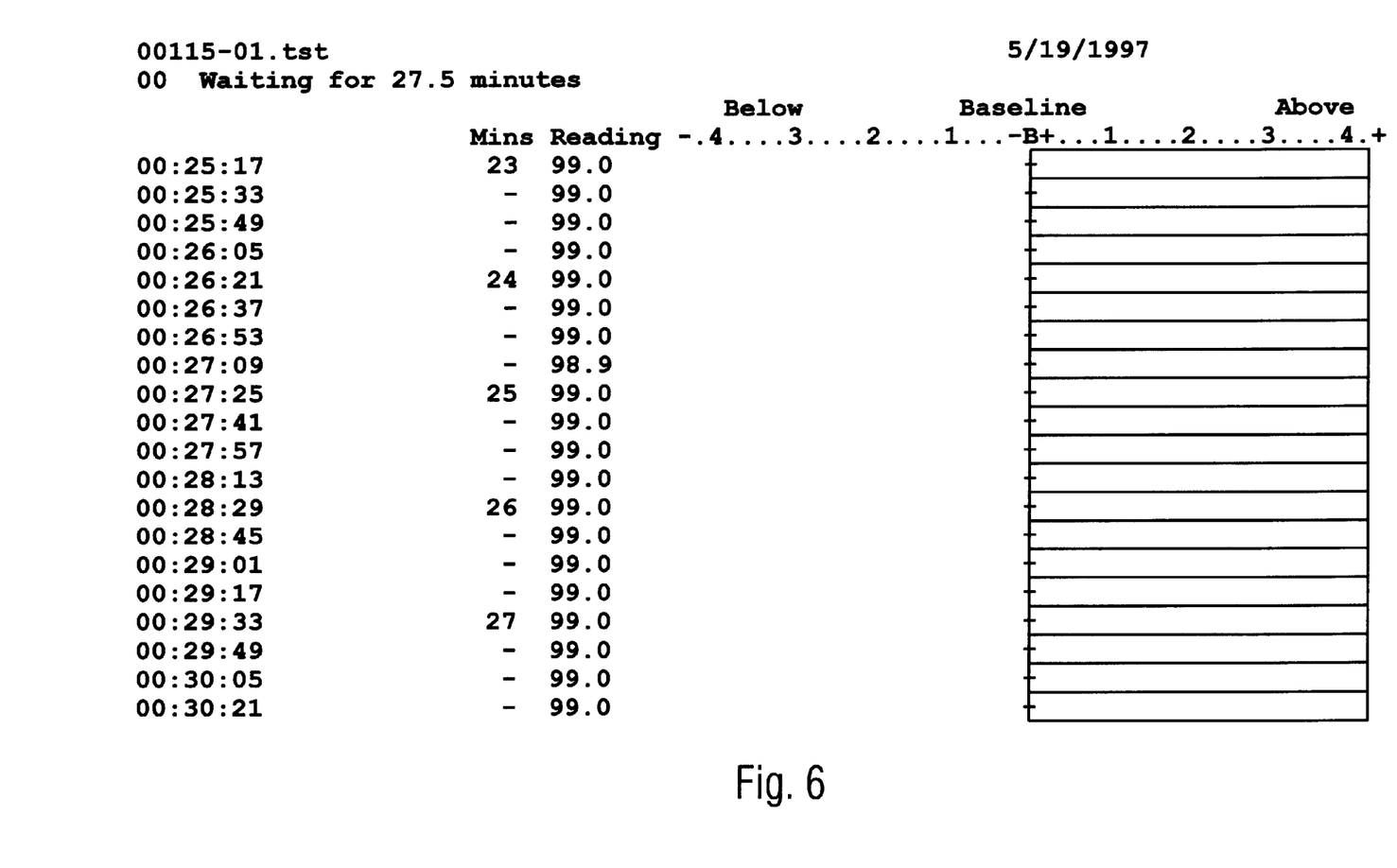
FIG. 6 is the temperature stabilization period screen showing the stabilized temperature readings of the subject.

The first 27.5 minutes of the test comprises a temperature stabilization period in which the subject's body temperature is allowed to stabilize in the testing site's environment. If at block 63 less than 27.5 minutes have elapsed since the start of the test, the process is returned to block 53. The initial portion of the stabilization period is shown in FIG. 5, in which the subject's body temperature is clearly fluctuating. If 27.5 minutes or more have elapsed at block 63, but less than 30 minutes have elapsed at block 64, the number of changes or fluctuations in the 10 previously saved temperature readings is checked at block 65. A fluctuation is a 0.1 degree or more difference between two consecutively recorded temperature readings. E.g., in the first 5 temperature readings shown in FIG. 5, there are 2 changes: 1 change from 97.9 to 98.0, 0 change from 98.0 to 98.0, 1 change from 98.0 to 98.1, and 0 change from 98.1 to 98.1. If there were more than 2 fluctuations, the subject's temperature has not sufficiently stabilized, so that process is returned to block 53. If there were 2 or fewer fluctuations at block 65, then the subject's temperature has stabilized enough. The final portion of the stabilization period is shown in FIG. 6, where there is no fluctuation in the subject's body temperature, which has clearly stabilized. A supplement is then selected at block 66 for testing, and the base temperature and stored temperatures on screen are reset to zero. If 30 minutes or more have elapsed since the start of the stabilization period at block 64, a supplement is automatically selected for testing, regardless of any fluctuations in the subject's temperature. The stabilization period is thus at least 27.5 minutes, but not more than 30 minutes.

Figure 4:
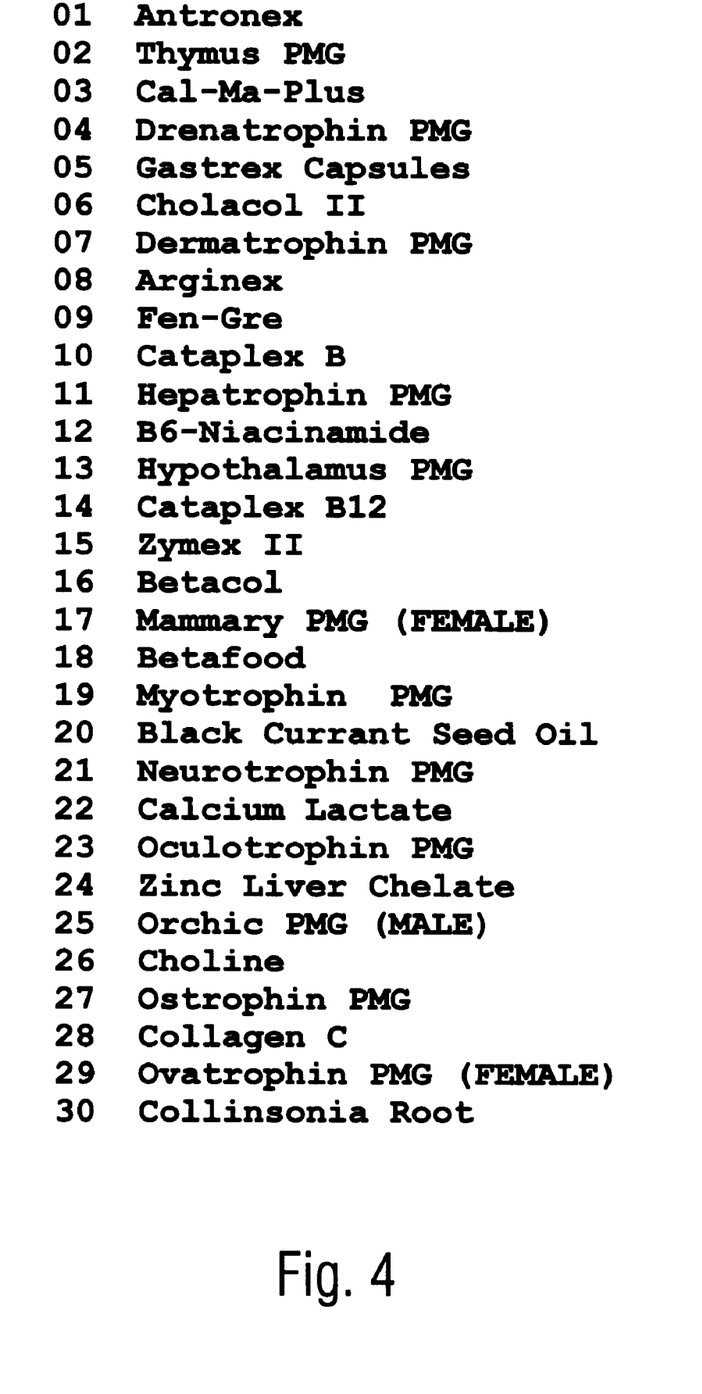
FIG. 4 is a partial list of selected nutritional supplements for testing.

An exemplar list of supplements selected for testing is shown in FIG. 4. The list may contain other supplements, and any total number of supplements. After the first supplement is selected for testing at block 66, the process is returned to block 53, and blocks 54–61 are repeated. Since a supplement is confirmed as being tested at block 61, the process is continued at block 67. If less than 1.5 minutes have elapsed since the start of a supplement testing period, the current temperature is saved at block 68, and the process is returned to block 53. If more than 1.5 minutes have elapsed since the start of the testing period, an audible alert or beep is produced at block 69 to prompt the subject to discard the supplement and take a sip of water. If 3 minutes or less have elapsed since the start of the testing period at block 70, the process is returned to block 53 to allow a minimum period of time for the supplement's effect to stabilize. If 3 minutes or more have elapsed since the start of the testing period at block 70, but less than 8 minutes have elapsed at block 71, the number of fluctuations in the 10 previously saved temperature readings are checked at block 72. If there are 3 or fewer fluctuations, the supplement has either little or no effect on the present subject, or its effect has faded sufficiently, so the process is continued at block 66, where the next supplement is selected for testing. If 8 minutes or more have elapsed since the start of the present testing period at block 71, the process is continued at block 66, where the next supplement is selected for testing. The testing period for each supplement is thus begun when the supplement is administered. The supplement is discarded at 1.5 minutes into its testing period, which is ended after at least 3 minutes, or at most 8 minutes. All the supplements are sequentially tested in the same manner. After the test, the saved temperature readings are uploaded to an evaluation center (block 40 in FIG. 2), where they are analyzed by a health professional.

Figure 7:
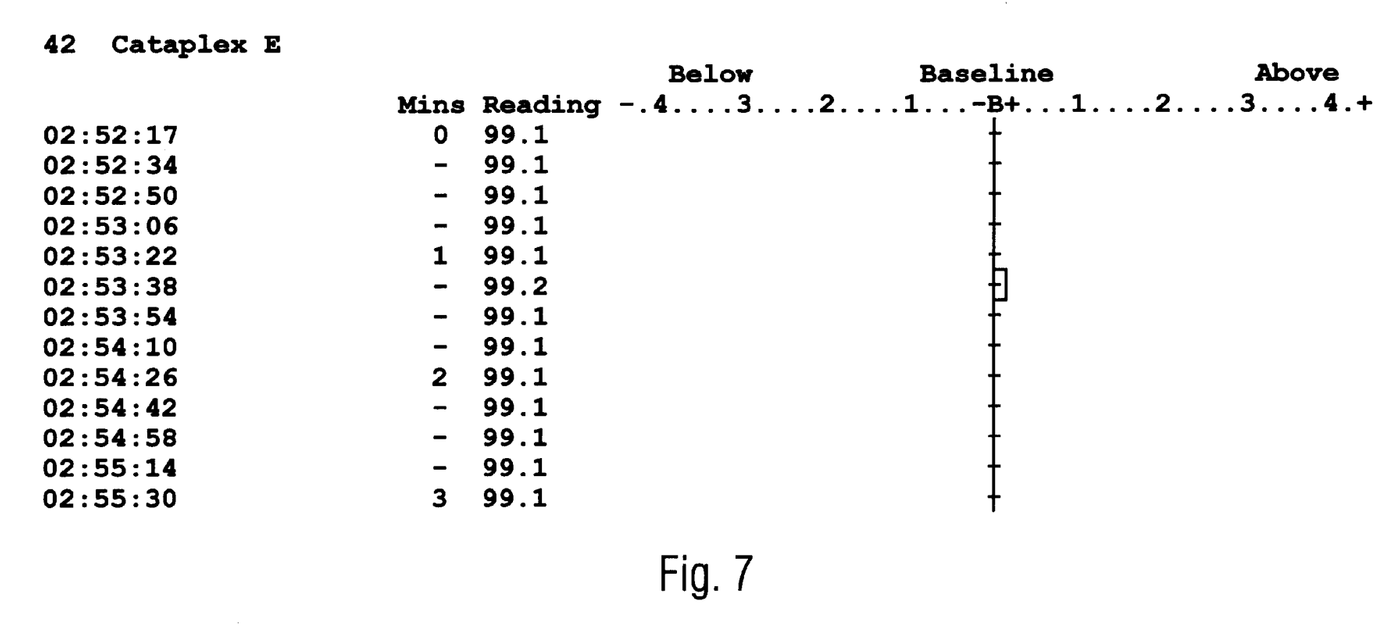
FIG. 7 is a testing screen showing an inactive response to a first nutritional supplement.
Figure 8:
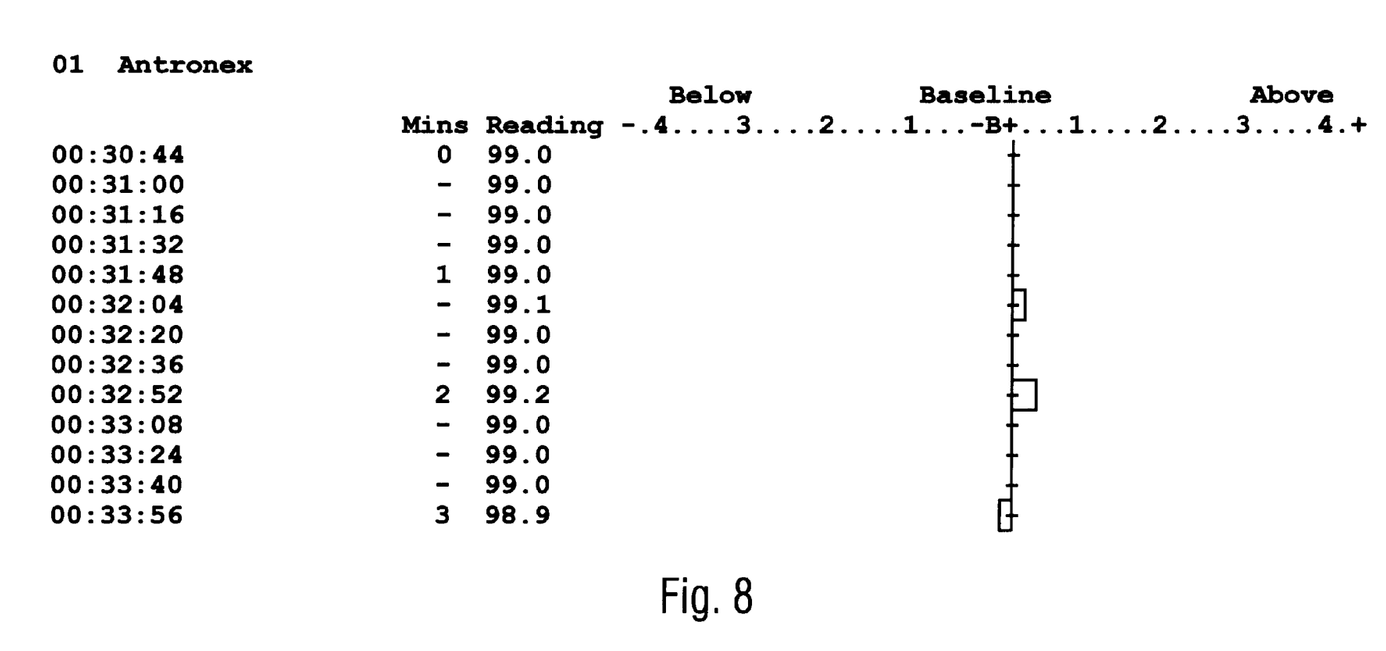
FIG. 8 is a testing screen showing a normal response to a second nutritional supplement.
Figure 9:
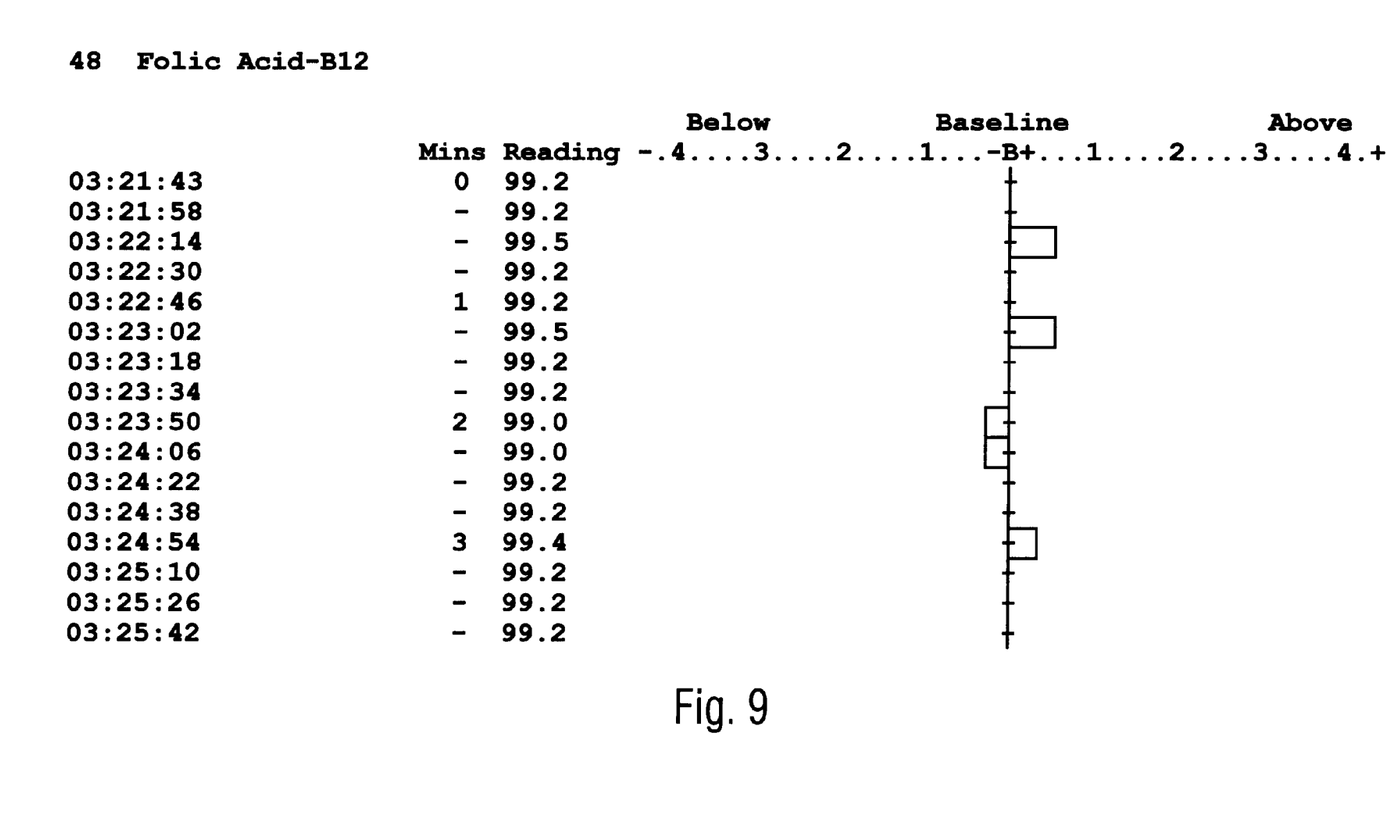
FIG. 9 is a testing screen showing an active response to a third nutritional supplement.

An example of an inactive response to a supplement is shown in FIG. 7. The supplement is causing little or no metabolic or physiological response in the subject, which is reflected in the low number of temperature fluctuations, e.g., 3 or fewer fluctuations, so that there is probably no nutritional need for it. An example of a normal response to a supplement is shown in FIG. 8. The supplement is causing a normal level of metabolic or physiological response in the subject, which is reflected in a normal number of temperature fluctuations, e.g., 3 fluctuations, so that there is still probably no nutritional need for it. An example of an active response to a supplement is shown in FIG. 9. The supplement is causing a high level of metabolic or physiological response in the subject, which is reflected in the high number of temperature fluctuations, e.g., more than 3 fluctuations, so that there is probably a nutritional need for it. I.e., a subject's need for a supplement is generally proportional to the number of body temperature fluctuations it causes in the subject. Nutritional deficiencies are thus methodically detected, and may be remedied by changing the subject's diet, or by taking nutritional supplements.

SUMMARY AND SCOPE

Accordingly, a nutritional deficiency identification system has been provided. It identifies the nutritional needs or deficiencies of a subject, so that they can be remedied by taking appropriate measures.

Although the above description is specific, it should not be considered as a limitation on the scope of the invention, but only as an example of the preferred embodiment. Many substitutes and variations are possible within the teachings of the invention. For example, any of the numeric parameters can be changed, such as the minimum temperature change that is considered to be a fluctuation, the length of the time periods, the number of temperature fluctuations that are considered as an inactive, normal, or active response, etc. Each supplement can be held on the tongue for its entire testing period. Instead of being performed by a health professional, the analysis can be performed by the computer with additional programming. The biofeedback instrument can be incorporated into the personal computer as an expansion board, or the computer can be incorporated into the biofeedback instrument as an embedded system. The biofeedback instrument can be eliminated if the temperature sensor provides a digital output that is connectable to a communication port of the computer. Therefore, the scope of the invention should be determined by the appended claims and their legal equivalents, not by the examples given.

I claim:

1. A nutritional deficiency identification method, comprising the steps of:

administering a nutritional supplement to a subject;

detecting body temperature fluctuations in said subject after said nutritional supplement is administered; and determining a need for said nutritional supplement based on said temperature fluctuations: said nutritional supplement is generally needed if a relatively high number of said body temperature fluctuations are detected, and said nutritional supplement is generally not needed if a relatively low number of said body temperature fluctuations are detected.

2. The nutritional deficiency identification method of claim 1, wherein said relatively high number of said body temperature fluctuations comprise more than about three fluctuations of at least about 0.1 degree each, and said relatively low number of said body temperature fluctuation comprise less than about three fluctuations of at least about 0.1 degree each.

3. The nutritional deficiency identification method of claim 1, further including recording said body temperature fluctuations at regular intervals.

4. The nutritional deficiency identification method of claim 1, further including recording said body temperature fluctuations at regular intervals, said relatively high number of said body temperature fluctuations comprise more than about three recorded fluctuations of at least about 0.1 degree each, and said relatively low number of said body temperature fluctuations comprise less than about three recorded fluctuations of at least about 0.1 degree each.

5. The nutritional deficiency identification method of claim 1, further including waiting for a body temperature of said subject to generally stabilize in a testing environment before administering said nutritional supplement to said subject.

6. The nutritional deficiency identification method of claim 1, further including removing said nutritional supplement from said subject after a predetermined period, and continuing to detect said body temperature fluctuations for another predetermined period.

7. A nutritional deficiency identification method, comprising the steps of:

sequentially administering a plurality of different nutritional supplements to a subject;

detecting body temperature fluctuations in said subject after each of said nutritional supplements is administered;

removing an already administered supplement from said subject;

waiting for a predetermined period to allow an effect of said already administered supplement to generally dissipate;

repeating the previous steps until all of said nutritional supplements are tested; and determining a need for each of said nutritional supplements based on corresponding body temperature fluctuations: any one of said nutritional supplements is generally needed if a relatively high number of corresponding body temperature fluctuations are detected, and any one of said nutritional supplements is generally not needed if a relatively low number of corresponding body temperature fluctuations are detected.

8. The nutritional deficiency identification method of claim 7, wherein said relatively high number of said body temperature fluctuations comprise more than about three fluctuations of at least about 0.1 degree each, and said relatively low number of said body temperature fluctuations comprise less than about three fluctuations of at least about 0.1 degree each.

9. The nutritional deficiency identification method of claim 7, further including waiting for a body temperature of said subject to generally stabilize in a testing environment before administering said nutritional supplements to said subject.

10. The nutritional deficiency identification method of claim 7, further including recording said body temperature fluctuations at regular intervals.

11. The nutritional deficiency identification method of claim 7, further including recording said body temperature fluctuations at regular intervals, said relatively high number of said body temperature fluctuations comprise more than about three recorded fluctuations of at least about 0.1 degree each, and said relatively low number of said body temperature fluctuations comprise less than about three recorded fluctuations of at least about 0.1 degree each.

12. A nutritional deficiency identification system, comprising:

a temperature sensor for measuring a body temperature of a subject; and a computer connected to said temperature sensor, said computer including instructions for:

prompting for sequential administration to said subject a plurality of different nutritional supplements;

detecting body temperature fluctuations representing nutritional needs in said subject after each of said nutritional supplements is administered;

prompting for an already administered supplement to be removed from said subject after a predetermined first period;

waiting for a predetermined second period to allow an effect of said already administered supplement to generally dissipate; and repeating the previous instructions until all of said nutritional supplements are tested.

13. The nutritional deficiency identification system of claim 12, further including a biofeedback instrument connected between said temperature sensor and said computer.

14. The nutritional deficiency identification system of claim 12, wherein said instructions further include waiting for said body temperature of said subject to generally stabilize in a testing environment before prompting for the sequential administration of said nutritional supplements to said subject.

15. The nutritional deficiency identification system of claim 12, wherein said instructions further include recording said body temperature fluctuations at regular intervals when detecting said body temperature fluctuations.

* * * * *